(12) United States Patent
Giovannini et al.

(10) Patent No.: US 12,314,278 B2
(45) Date of Patent: *May 27, 2025

(54) SCALABLE VISUAL ANALYTICS PIPELINE FOR LARGE DATASETS

(71) Applicant: International Business Machines Corporation, Armonk, NY (US)

(72) Inventors: Andrea Giovannini, Zurich (CH); Joy Tzung-yu Wu, San Jose, CA (US); Tanveer Syeda-Mahmood, Cupertino, CA (US); Ashutosh Jadhav, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,368

(22) Filed: Dec. 14, 2023

(65) Prior Publication Data

US 2024/0111777 A1 Apr. 4, 2024

Related U.S. Application Data

(63) Continuation of application No. 17/472,787, filed on Sep. 13, 2021, now Pat. No. 11,928,121.

(51) Int. Cl.
*G06F 16/2458* (2019.01)
*G06F 16/248* (2019.01)
(Continued)

(52) U.S. Cl.
CPC ........ *G06F 16/2474* (2019.01); *G06F 16/248* (2019.01); *G06F 16/9024* (2019.01); *G16H 10/60* (2018.01)

(58) Field of Classification Search
None
See application file for complete search history.

(56) References Cited

U.S. PATENT DOCUMENTS 6,222,540 B1 4/2001 Sacerdoti
9,424,669 B1 8/2016 Lu et al.
(Continued)

OTHER PUBLICATIONS

List of IBM Patents or Patent Applications Treated as Related, Dec. 13, 2023, 2 pages.

(Continued)

*Primary Examiner* — Dawaune A Conyers
(74) *Attorney, Agent, or Firm* — Harrity & Harrity, LLP

(57) ABSTRACT

Mechanisms are provided to implement a visual analytics pipeline. The mechanisms generate, from an input database of records, a chronology-aware graph data structure of a plurality of records based features specified in an ontology data structure. The chronology-aware graph data structure has vertices representing one or more of events or records based features corresponding to events, and edges representing chronological relationships between events. The mechanisms execute a chronology-aware graph query on the chronology-aware graph data structure to generate a filtered set of vertices and corresponding features corresponding to criteria of the chronology-aware graph query. The mechanisms execute a pattern discovery operation on the filtered set of vertices and corresponding features to identify a subset of vertices and corresponding features that correspond to a relatively higher frequency set of patterns of event paths, and generate a visual analytics graphical representation for the subset of vertices and corresponding features.

20 Claims, 10 Drawing Sheets

(51) Int. Cl.
*G06F 16/901* (2019.01)
*G16H 10/60* (2018.01)

(56) References Cited

U.S. PATENT DOCUMENTS

| | | |
|---|---|---|
| 9,690,861 B2 | 6/2017 | Boloor et al. |
| 10,452,961 B2 | 10/2019 | Hu et al. |
| 10,861,202 B1 | 12/2020 | Agnew et al. |
| 10,877,984 B1 | 12/2020 | Martino et al. |
| 11,016,649 B2 | 5/2021 | Slawinski et al. |
| 2011/0099500 A1 | 4/2011 | Smith et al. |
| 2012/0221553 A1 | 8/2012 | Wittmer et al. |
| 2013/0290005 A1 | 10/2013 | Vesto et al. |
| 2013/0332194 A1 | 12/2013 | D'Auria et al. |
| 2014/0022255 A1 | 1/2014 | Barbouche et al. |
| 2014/0108380 A1 | 4/2014 | Gotz et al. |
| 2014/0257847 A1 | 9/2014 | Hu et al. |
| 2015/0161332 A1 | 6/2015 | Simms, Jr. et al. |
| 2017/0046602 A1 | 2/2017 | Hu et al. |
| 2018/0098737 A1 | 4/2018 | Villazon-Terrazas et al. |
| 2021/0134418 A1 | 5/2021 | Frieder et al. |
| 2023/0048252 A1* | 2/2023 | Sasidharan ............ G16H 50/20 |
| 2023/0083916 A1 | 3/2023 | Giovannini et al. |

OTHER PUBLICATIONS

Rostamzadeh, Neda et al., "Visual Analytics for Electronic Health Records: A Review", Informatics. 2021; 8(1):12. https://doi.org/10.3390/informatics8010012, Feb. 23, 2021, 31 pages.

Rostamzadeh, Neda, "Visual Analytics for Performing Complex Tasks with Electronic Health Records", Electronic Thesis and Dissertation Repository, 7617, Western University, 212 pages, Feb. 2021.

* cited by examiner

```
function RETRIEVE_PATH(vertex_to_explore)
    next_vertices = get_out_vertices(vertex)
    for next_vertex in next_vertices do
        if vertex_type(next_vertex) = encounter then
            if next_vertex ≠ END_V and $t_{encounter} - t_{start}$ <= max, then
                Insert next_vertex into stored_paths
                RETRIEVE_PATH(next_vertex)
            else
                return stored_paths and stored_neighbors
            end if
        else
            Insert next_vertex into stored_neighbors
        end if
    end for
    return stored_paths and stored_neighbors
end function
```

FIG. 3

```
Start with filtered_vertices = [START_V]
for layer in range($n_{layers}$) do
    for vertex in filtered_vertices do
        Find all_neighbors of vertex as tuple (neighbor, edge_weight(vertex, neighbor))
        Rank neighbors in descending order based on edge_weight
        Select top $n_l$(layer) and store
    end for
    Update filtered_vertices with neighbors stored for layer
end for
Remove vertices not contained in the filtered_vertices stored during the iterations
```

FIG. 4

SCALABLE VISUAL ANALYTICS PIPELINE FOR LARGE DATASETS

BACKGROUND

The present application relates generally to an improved data processing apparatus and method and more specifically to computer mechanisms for providing a scalable visual analytics pipeline for large datasets. The scalable visual analytics pipeline may be part of, or otherwise operate in conjunction with, a decision-support system or other cognitive computing system, for example.

Decision-support systems exist in many different industries where human experts require assistance in retrieving and analyzing information. An example is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to specifically configure the at least one processor to implement a visual analytics pipeline that performs the method. The method comprises generating, from an input database of records, a chronology-aware graph data structure of a plurality of records based features specified in an ontology data structure. The chronology-aware graph data structure comprises vertices representing one or more of events or records based features corresponding to events, and edges representing chronological relationships between events. The method also comprises executing a chronology-aware graph query on the chronology-aware graph data structure to generate a filtered set of vertices and corresponding features corresponding to criteria of the chronology-aware graph query. The method further comprises executing a pattern discovery operation on the filtered set of vertices and corresponding features to identify a subset of vertices and corresponding features that correspond to a relatively higher frequency set of patterns of event paths. In addition, the method comprises generating a visual analytics graphical representation for the subset of vertices and corresponding features in a visual analytics output.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 3 is an example diagram of a chronology-aware graph query (CGQ) algorithm implemented by CGQ logic of a CGQ engine in accordance with one illustrative embodiment;

FIG. 4 is an example diagram of a pattern discovery algorithm implemented by pattern discovery logic of a pattern discovery and visualization engine in accordance with one illustrative embodiment;

DETAILED DESCRIPTION

Figure 1:
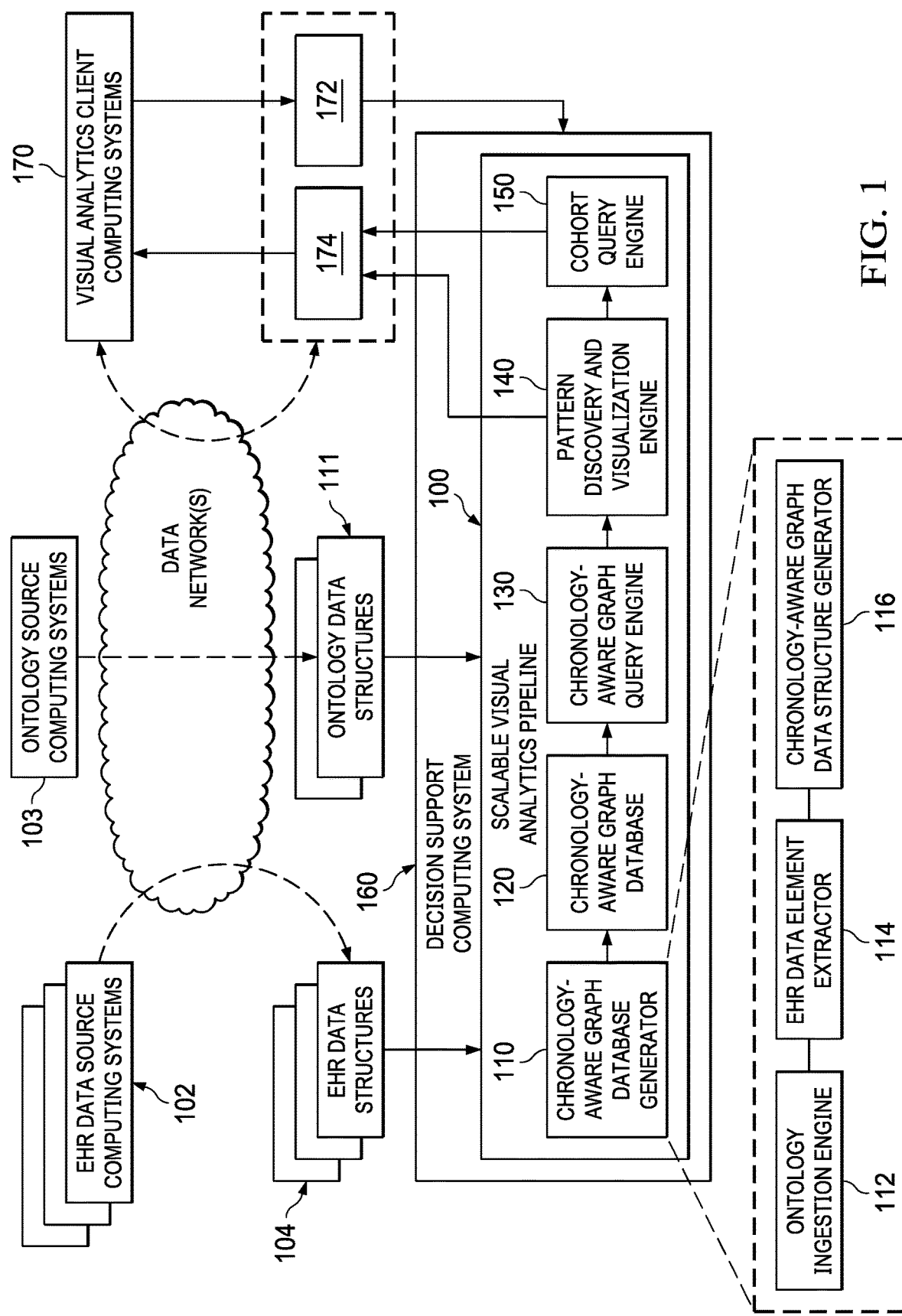
FIG. 1 is an example block diagram illustrating the primary operational elements of a scalable visual analytics pipeline in accordance with one illustrative embodiment.

Decision-support system operations are dependent on the digitization of health information and the implementation of computer tools to assist with understanding the patterns and correlations present in the voluminous, and often complex, information present in the digitized health information. One key drive for the digitalization of health information from routine care delivery is to facilitate better understanding of the large variations in health care delivery practices, costs, and patient outcomes across health systems and patient populations. Traditionally, epidemiology is a resource consuming study of diseases, risk factors and outcomes by comparing different patient population cohorts. Some of this knowledge can quickly become outdated as underlying health risk exposures and medical practices change across time. Automated data processing mechanisms to quickly re-validate or discover new relationships between emerging diseases, risk factors, management practices and patient outcomes would add tremendous value to digitalized health data and digital health data based research and patient treatment computing systems, such as artificial intelligence and machine learning based systems, decision support systems, and the like. Such automated data processing mechanisms would also require chronology awareness, as the evaluation of temporal relationships is crucial to discovering potential causal or risk factor correlations between clinical data points when comparing patient cohorts.

By using large scale digitalized datasets, higher and higher powered machine learning tools may be used to automatically learn the underlying data patterns to perform various disease prediction and/or clustering tasks, as well as such prediction and/or clustering tasks for other domains, such as or resource utilization prediction/clustering and the like (for purposes of the present description, it will be assumed that the mechanisms of the illustrative embodiments are employed in the medical domain, but are not limited to such). However, it is often the case that such machine learning operations are performed without an adequate understanding of the interaction between data points and the processes under which the data was collected. As a result, these machine learning mechanisms learn to make predictions using spurious correlations that have no direct feasible causality when one consults a domain expert, such as a clinical domain expert. On the other hand, clinicians also cannot easily inspect these underlying data patterns from just tabular data, or even worse, a large volume of free-form texts.

Visual Analytics offers a way to include domain experts in the loop for the task of analyzing the clinical characteristics and care path differences between patient cohorts that may explain different outcomes downstream. However, healthcare-focused visual analytics tools only either visualize patient data points at one cross-sectional time point for different modalities of health data (e.g., age, sex, diseases, labs, etc.), or present longitudinal time series line graphs for tracking mostly numerical data points (e.g., blood pressure, labs, etc.). Such visual analytics work well for dashboard understanding of individual patient health status and can easily be queried from tabular databases. However, these visualizations are limited for the clinical use case of aiding the discovery of potential causal or risk factor level correlations between, for example, differences in management and patient outcomes, especially across a large group of patients, or various cohorts of patients. Such understanding needs a visualization of clinical or care pathways that both presents the chronology of events and has the flexibility and efficiency to create clinical comparison cohorts from a range of different epidemiological style interactive-queries.

A clinical or care pathway is a multi-disciplinary management tool based on evidence-based medical practice for a group of patients with a predictable clinical course, in which the different interventions by medical professionals involved in the patient care are defined, optimized, and sequenced according to a particular desired chronology, with outcomes tied to specific interventions. Put more simply, with regard to the chronology-aware graph data structure mechanisms of the illustrative embodiments, a care pathway, or simply "path", is a chronological sequence of patient encounters and their results, i.e., interactions between a patient and a medical practitioner and/or medical facility for purposes of administering medical care to the patient, along with the feature instances associated with those patient encounters. It should be appreciated that a care pathway may be defined a priori by one or more medical experts, while an actual path, or care pathway instance, may be extracted as an observation from the reality of the patient data. The extracted actual path or care pathway instance may deviate from the medical expert defined care pathways.

One of the main technical challenges that existing mechanisms have, is the large number of medical features present for such machine learning, on the order of hundreds of thousands. This combined with electronic health records (EHR) data samples with hundreds of encounters spanning years, leads to a large and practically unmanageable number of possible patterns to explore, e.g., through frequent sequence mining, exceeding billions of possible patterns.

The illustrative embodiments address these above issues by providing an improved computing tool solution based on an improved chronology-aware EHR database and improved graph-based mechanisms to perform data mining operations to mine the possible patterns in the features of the EHR input data. The illustrative embodiments provide mechanisms for generating an explicit chronological graph representation of patient healthcare trajectories from EHR data. The illustrative embodiments further provide improved computing tool mechanisms that operate to express a range of common epidemiological style health pattern discovery questions, provide mechanisms to efficiently retrieve patient care pathways, and mechanisms that are capable of handling tens of thousands of patients with historical data spanning across years. Moreover, the illustrative embodiments provide a graph-based visual analytics pipeline that presents query results across time as graph visualization diagrams, e.g., Sankey Graph Visualization (SVG) diagrams, which allow interactive pattern discovery for domain experts.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a compute, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides a scalable graph based visual analytics (VA) pipeline that can operate on large electronic health record (EHR) databases having hundreds, thousands, or tens of thousands of features. The illustrative embodiments provide an explicit chronological graph representation of patient healthcare trajectories from EHR databases. The illustrative embodiments can express a range of common epidemiological style health pattern discovery questions and can more efficiently retrieve patient care pathways than other query language based systems, e.g., SQL systems. The illustrative embodiments can handle tens of thousands of patients with historical data spanning across years. The illustrative embodiments provide a graph-based visual analytics pipeline that presents the query results across time as a graph visualization diagram to allow interactive pattern discovery for domain experts.

FIG. 1 is an example block diagram illustrating the primary operational elements of a scalable visual analytics pipeline in accordance with one illustrative embodiment. To illustrate the operation of the primary operational elements according to the illustrative embodiments, the following description will utilize an example medical condition referred to as a Transient Ischaemic Attack (TIA), or "mini stroke", as a case study. TIA is caused by a temporary disruption in the blood supply to part of the brain where the neurological symptoms fully resolve after the event. However, TIA is regarded as an early warning sign that a patient may be at risk of having a full blown life-changing event, such as a stroke, death, or another cardiovascular related event.

As shown in FIG. 1, the scalable visual analytics pipeline 100 comprises a chronology-aware graph database generator 110, a chronology-aware graph database 120, a chronology aware-graph query (CGQ) engine 130, a pattern discovery and visualization engine 140, and a cohort query engine 150. It should be appreciated that while these specific elements are shown in FIG. 1, the scalable visual analytics pipeline 100 may comprise additional logic elements not explicitly shown and which provide underlying computer functionality and capabilities upon which the depicted elements are built, e.g., operating system logic, device drivers, communication interface logic, etc.

The elements of FIG. 1 may be implemented as automated computer logic that comprises one or more of software logic and/or hardware logic specifically configured to perform the operations and functionality attributed to these elements in the present description in accordance with one or more of the illustrative embodiments. With regard to software logic, this logic is executed on computer hardware to specifically configure the computer hardware to perform the operations and functionality described herein. With regard to hardware logic implementations of one or more of the operations or functionality described, if utilized, this hardware logic may be implemented, for example, as application specific integrated circuits (ASICs) or other circuitry or physical hardware specifically configured to perform the described operations/functionality. Regardless of whether or not hardware logic, software logic, or any combination of hardware logic and software logic is utilized, the resulting computing device(s) are specifically configured to be specific computing device(s) that perform the specific operations/functionality described herein.

The chronology-aware graph database generator 110 comprises logic to generate, for each patient in an EHR database source, one or more patient centric graph data structure(s) having chronology awareness, which are stored in the corresponding chronology-aware graph database 120 for use by downstream logic of the pipeline 100 in generating analytics visualizations. The chronology-aware graph database generator 110 comprises an ontology ingestion engine 112, an EHR data element extractor 114, and a chronology-aware graph data structure generator 116. The ontology ingestion engine 112 ingests one or more ontology data structures 111, from one or more ontology source computing systems 103, that represent domain knowledge for a particular domain of the input database sources. The ontology source computing system(s) 103 may be any established source of ontology data structures specifying a relationship of concepts for a particular domain of interest, e.g., the Systematized Nomenclature of Human Medicine (SNOMED) clinical terms (CT)® computing systems provide ontology data structures for medical applications corresponding to the SNOMED CT standard promulgated by the United States of America federal government and required by the U.S. Healthcare Information Technology Standards Panel. SNOMED CT is owned and operated by SNOMED International, a non-profit organization.

The particular domain and corresponding ontology may have a level of specificity desirable for the particular implementation. For example, the domain may be a medical domain in one implementation, which comprises a large number of different potential features that may be extracted from EHR data in one or more EHR database sources. In other illustrative embodiments, the domain may be more specific, such as subgroups of one or more medical condition type patients, e.g., brain injuries, cardiac medical conditions, cancer, etc. As noted above, while the illustrative embodiments will be described with regard to patients and the medical domain, the illustrative embodiments are not limited to such and may be applied to other domains outside the medical field, such as resource utilization domains, or the like. In general, the illustrative embodiments can be applied to any data with a temporal dimension associated to the data samples. As one further example, mechanisms of the illustrative embodiments may be implemented with regard to information technology (IT) support data samples with their associated temporal features, such as where servers or server components are analogous to patients in the present description, and the events logged by the servers or server components are analogous to the patient encounters discussed herein. Thus, for example, in an IT implementation of the illustrative embodiments, a plurality of records may be a plurality of information technology records, such as log records or the like, specifying events occurring in an information technology environment, and the events themselves may be information technology environment events occurring within one or more information technology software or hardware systems.

The ontology data structure(s) 111 for the given domain specify the types of features and their relationships that may be extracted from the input EHR data structures 104 of the input database sources, e.g., EHR data source computing system(s) 102. In the example illustrative embodiments, the domain being a medical domain and specifically a medical domain for the medical condition referred to as a Transient Ischaemic Attack (TIA), or "mini stroke", the ontology data structure(s) 111 specify the features that may be extracted from patient EHR data structures 104 comprising entries for patient features as well as encounter features, where the encounter features are features corresponding to encounters between the patient and one or more medical personnel or medical facilities. The ontology data structure(s) 111 may further include one or more ontology data structures specifying general features of the patient that are to be extracted from patient EHR data structures 104, such as patient name, address, age, gender, race, and various other types of demographics including, but not limited to, height, weight, etc. The patient EHR data structures 104 may be obtained from any source computing systems 102 which store such databases of patient EHR data, such as various healthcare databases maintained by governmental and/or healthcare provider organizations, medical facilities, doctors' offices, and the like.

The ontology ingestion engine 112 ingests the one or more ontology data structure(s) 111 for the particular domain and configures the EHR data element extractor 114 to extract data elements, from input EHR data structures 104 from one or more EHR database source computing systems 102, which correspond to the features specified in the one or more ontology data structure(s) 111. The EHR data element extractor 114 may implement logic for extracting data elements corresponding to ontology data structure 111 specified features from structured and/or unstructured EHR data structures. For example, the EHR data element extractor 114 may operate on table based or otherwise structured EHR data structures 104 to identify fields having labels or annotations corresponding to the features specified in the ontology data structure 111 and the corresponding data elements may be retrieved. In cases where the EHR data structures 104 include unstructured content, such as natural language content, the EHR data element extractor 114 may configure and implement computerized natural language processing logic and/or other artificial intelligence machine learning computing techniques to identify portions of the natural language content of the EHR data structures 104 that correspond to features specified in the ontology data structure 111, e.g., by annotating the natural language content with labels or annotations corresponding to their corresponding ontology features based on a machine learning or artificial intelligence based classification of syntax and semantics of the natural language content, and using the annotations to select data elements corresponding to features specified in the ontology data structure 111. Of course, other types of analysis of EHR data structures 104 to extract data elements corresponding to features of interest, as may be specified in the ontology data structure(s) 111, as will be apparent to those of ordinary skill in the art in view of the present description, may be used without departing from the spirit and scope of the present invention.

The extracted data elements are correlated with the feature types and are used to generate chronology-aware graph data structures corresponding to the patients. That is, the EHR data element extractor 114 extracts, for each patient in the input database, such as from a source computing system 102, the data element instances of the features specified in the ontologies 111. These data element instances and their mappings to features in the ontologies 111 are then input to the chronology-aware graph data structure generator 116 which generates the chronology-aware data structure, which may be a graph based data structure, from these data element instances and feature mappings, which is then stored in the chronology-aware graph database 120.

The chronology-aware graph data structure generator 116 comprises logic to identify the data element instances of features and their relationships to patients and medical personnel/medical facility encounters with the patient (hereafter referred to as simply "encounters"). Thus, for example, the ontology data structure(s) 111 may indicate that patients having a certain set of features defining the patient including, but not limited to, a name, address, birth date, gender, age, race, height, weight, socio-economic level (such as an economic range for annual income, for example). Similarly, the ontology data structure(s) 111 may indicate that medical personnel/medical facility encounters with a patient have another set of features, such as medical codes for diagnosis, lab results, vital signs, symptoms, dates, times, etc. These different features may be used as a basis for extracting instances of these features, i.e., data elements matching the feature types specified in the ontology data structure(s) 111, from the EHR data structures 104. The temporal aspects of the extracted data elements corresponding to features may be maintained such that the data elements may be correlated with a temporal ordering of encounters and thereby provide a chronology awareness.

The chronology-aware graph data structure generator 116 generates, for a given patient in the input EHR data structures 104, a chronology-aware data structure based on these identified data element instances and their relationships in accordance with a chronology-aware patient-centric graph schema that organizes data elements and relationships relative to the patient, and encounters with the patient, in a chronological ordering. Data elements representing features of the patient are connected to a node representing the patient, and data elements representing features of the patient with regard to patient encounters are connected to nodes representing the various patient encounters. Each of the encounters are connected to the patient node by edges. The chronology of the encounters are modeled as directed edges between encounter nodes (or vertices) going from an oldest encounter node in the chronology to a newest encounter node. Such a chronology-aware data structure for a given patient may be generated for each patient in the input EHR data structures 104 of an input EHR database, such as may be maintained by a source computing system 102, such that a plurality of patients may have their EHR data structures 104 represented as corresponding chronology-aware data structures, which may be stored in a chronology-aware graph database 120. These chronology-aware data structures for each of the patients may be stored separately in the database 120 or may be combined into an overall chronology-aware data structure having multiple patient's extracted EHR data elements, but maintaining the association of the data elements with the particular patients to which they correspond.

In some illustrative embodiments, with regard to an example chronology-aware data structure representing a graph structure, one node (feature node) in the graph is provided per feature (for example an ontological concept), and each encounter (of each patient) that contains that feature will be linked with the feature node. This type of chronology-aware graph data structure allows for searching a given feature to identify all relevant encounters of all patients with one graph traversal. In other illustrative embodiments, multiple graphs are kept separated, where each graph contains a patient cohort. The advantage of these other illustrative embodiments is that searches can be launched in parallel over all graphs at the only price of duplicating the feature nodes in all the graphs.

The chronology-aware data structure representation of the data elements of the patient EHR data structures facilitates a more efficient searching of features of patients and patient encounters, making visual analytics and chronology-aware query processing possible. That is, by generating a chronology-aware data structure representation such as that of the illustrative embodiments, querying the feature instances of these chronology-aware data structure representations may be accomplished by a selective inference, i.e., searching for interesting patterns in data instead of having to perform multiple join operations per chronological step, as would be required in a common data model. That is, instead of navigating through a graph by blindly adding all the found nodes after each traversal, the illustrative embodiments provide mechanisms to perform a selective inference for every path and at every traversal step, with the selection conditions being based on, for example, temporal distance and resulting node metadata.

That is, having generated chronology-aware data structure representations, which may be represented as chronology-aware graphs, the chronology aware-graph query (CGQ) engine 130 may be employed to process chronology aware graph queries for patient encounters having feature instances (data elements) corresponding to specified ranges and combinations of such features instances. For example, in some illustrative embodiments, the chronology aware graph queries (CGQs) may be defined as part of a visual analytics request 172 by a user, such as via a graphical user interface or the like, associated with the scalable visual analytics pipeline 100 and/or decision support computing system 160 with which the pipeline 100 is associated. That is, the user may access the decision support computing system 160, via a visual analytics client computing system 170 and one or more data networks, e.g., the Internet, one or more LANs, one or more WANs, or the like, and interact with the decision support computing system 160 and scalable visual analytics pipeline 100 via one or more user interfaces to define queries of interest to the user. Alternatively, such queries may be automatically generated by a visual analytics client computing system 170 by way of an automated process. Whether user generated or automated process generated, the visual analytics request 172 generated may specify certain input parameters defining the chronology-ware graph query (CGQ) that is to be processed, such as a start and/or end vertex of patient care paths (a patient care path being a sequence of patient encounters and the feature instances associated with those encounters), a maximum time duration of the paths to be retrieved, a type of vertices (see examples in Table 1 hereafter), the length of edges, such as in terms of days, months, years, etc. (relative time between encounter vertices) (this is also referred to herein as the maximum time t), whether the chronology aware graph query is to be executed for encounters in the past and/or in the future, values for patient features of interest (where the "values" are also referred to as feature instances or data elements corresponding to features), such as age range and gender, for example, or any other combination of patient features of interest, as well as the number of vertices and edges to be included in the visual analytics graphical representation (or "visualization"). It should be appreciated that the visual analytics request 172 may also specify parameters for a cohort query to compare visual analytics representations for a plurality of cohorts of patient EHRs, as will be described in greater detail hereafter with regard to the cohort query engine 150.

Figure 5:
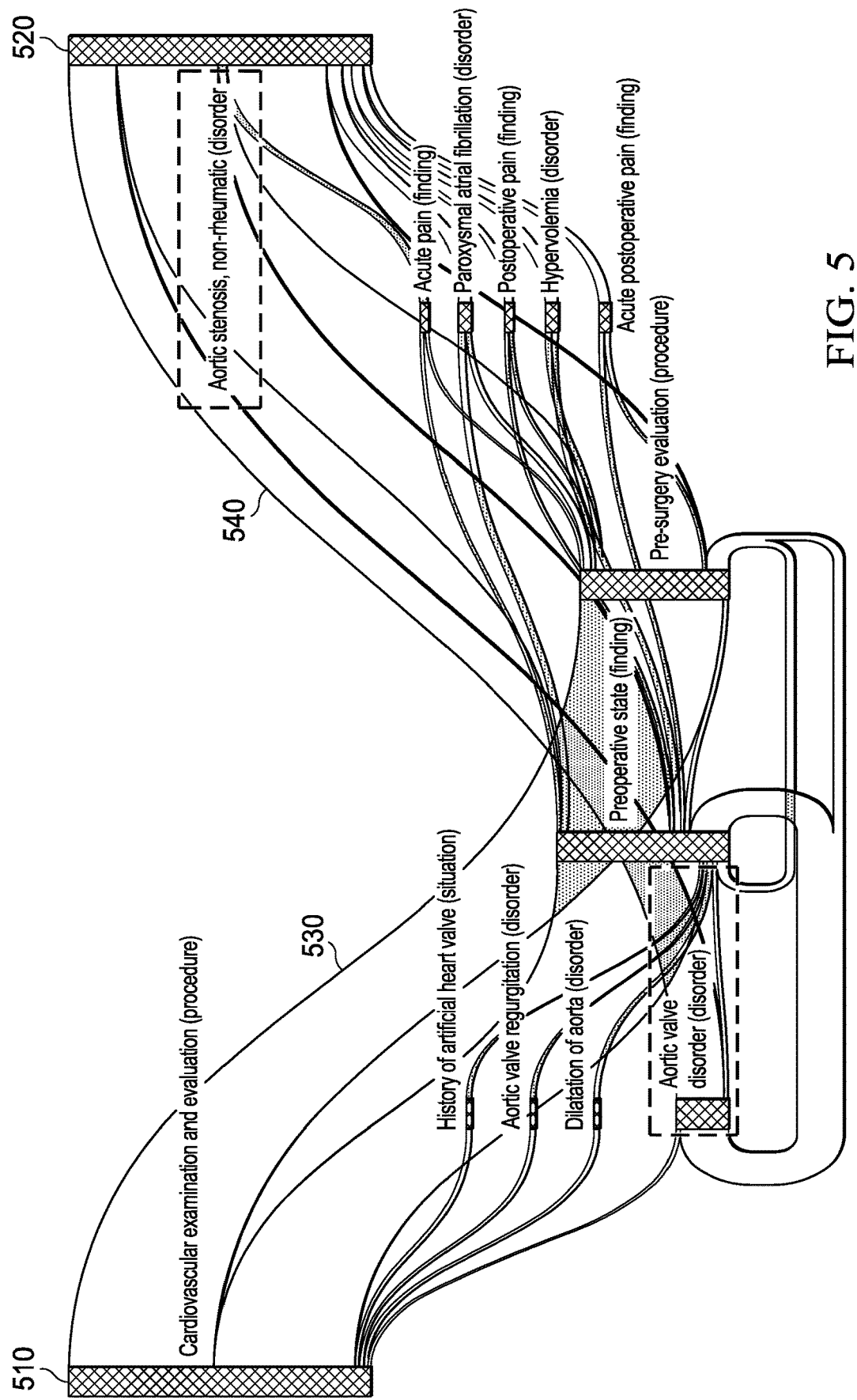
FIG. 5 is an example diagram of a visual analytics graphical representation for a coherent-aware graph query in accordance with one illustrative embodiment.

The chronology-aware graph queries (CGQs) operate to gather all the feature instances associated with patient encounters happening between the presence of a feature instance "START_V", where "START_V" specifies a starting vertex or node in the chronology-aware graph data structure for one or more patients, and a first occurrence of an end feature instance "END_V", where "END_V" specifies an ending vertex or node, for all patients within a maximum time period of t, which may be specified in days, weeks, or any other time frame desirable for the particular implementation. In gathering all the feature instances associated with such patients, the information specifying which patient is associated with which set of feature instances and the time when the feature instances were recorded is maintained. For example, as shown in the example of FIG. 5, START_V is "Cardiovascular examination and evaluation (procedure)" and END_V is the "Aortic stenosis, non-rheumatic (disorder). It should be appreciated that the CGQ may generate a visualization for a single patient or a cohort of patients and thus, the visual representation for visual analytics purposes may display more than one patient's information, such as with regard to epidemiological cohorts or the like.

The CGQ is executed by the CGQ engine 130 iteratively, for each vertex from the START_V vertex to the END_V vertex. The CGQ explores and looks at the vertices connected to the outputs of the selected vertex and determines: (1) if the next vertex along a path is an encounter vertex and is not the END_V, and (2) that the difference in time of the encounter corresponding to the encounter vertex and the start vertex time is less than a maximum time t. If both conditions are satisfied, then that vertex's feature instances are stored in the stored paths. If the next vertex along the path is not an encounter vertex, it is stored in a stored neighbors data structure. If the next vertex is the end vertex, END_V, or the time is beyond the maximum time t from the start vertex time, then the stored paths and the stored neighbors are returned. The "paths" are listings of node identifiers. Each listing of node identifiers in the "stored paths" describing which encounters were traversed for one path, with all encounters of the one path belonging to the same patient. The "stored neighbors" contains the information about which features were contained in which traversed encounters, where this feature information drives the visualization generated by the mechanisms of the illustrative embodiments. Both the stored paths and the stored neighbors are retrieved together for computational efficiency during the same graph traversal.

The CGQ allows for both a next encounter and features of a current encounter to be obtained during a same traversal of the chronology-aware graph data structures, e.g., the next encounter being identified in the stored paths and the features being stored in the stored neighbors, which improves the efficiency by which the evaluation is performed. For example, the CGQ is more efficient than common data format based database operations, such as SQL based operations, which would require multiple join operations to identify the next encounter and the features of the current encounter. It has been determined that the retrieval of paths using the CGQ mechanisms of the illustrative embodiments provide increased improvements in efficiency, e.g., reductions in computation time costs, as the number of features increases. That is, when chronological paths for large populations and long temporal windows have to be extracted, involving on the order of 10,000 features, CGQ shows up to a hundred-fold improvement in time cost over common data format based mechanisms.

As noted previously, the illustrative embodiments provide chronology-aware graph database mechanisms that generate chronology-aware data structures and store them in a database 120, based on a processing of electronic health records (EHRs) of patients obtained from EHR data structure source computing systems. The chronology-aware data structures may be represented as graph data structures and are obtained by the chronology-aware graph database mechanisms performing data transformation operations that transform data from a common data model used in the EHR data structure source computing systems, to a patient centric graph data structure that explicitly models the chronology of encounter events as edges.

Figure 2A:
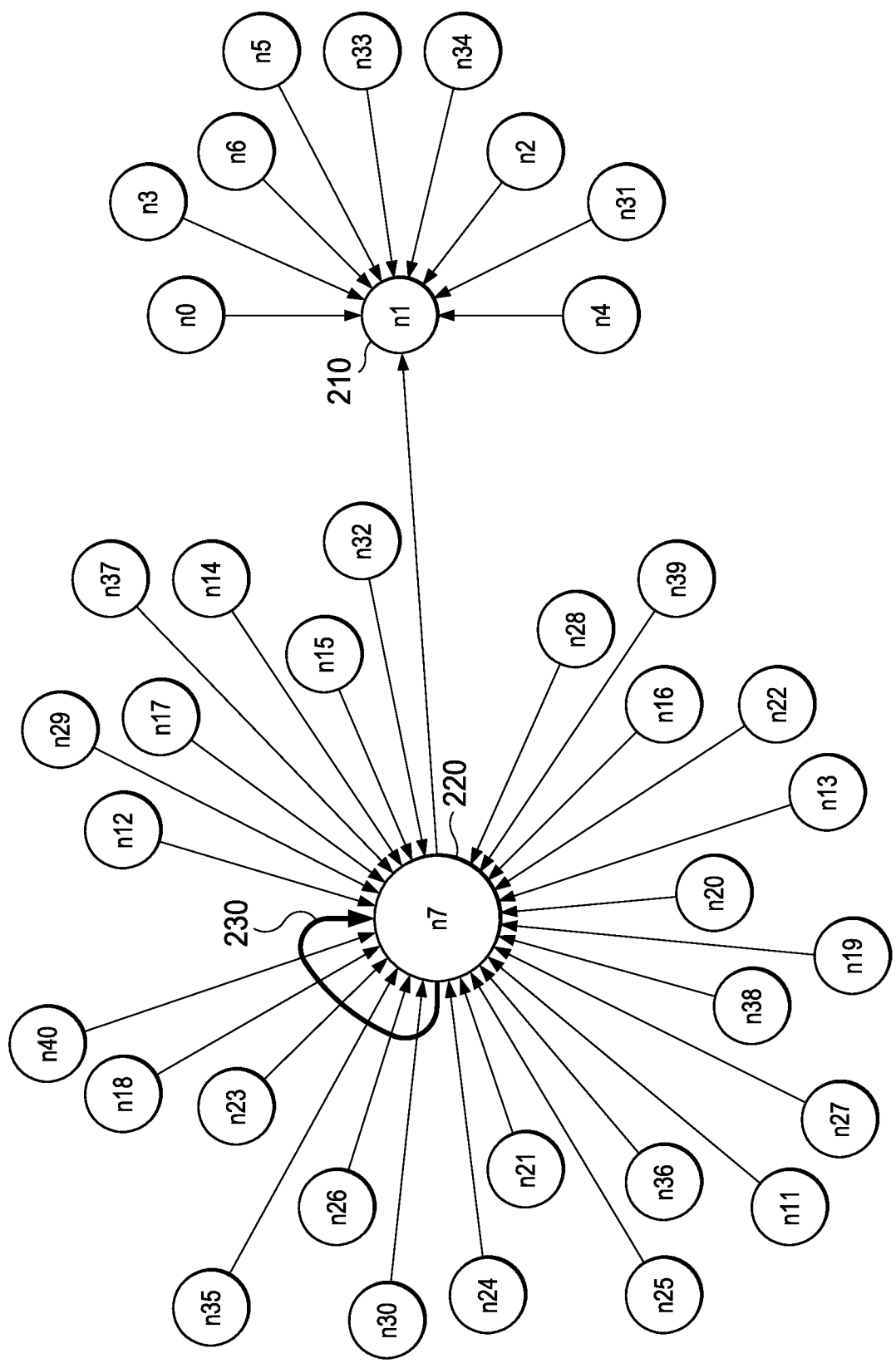
FIGS. 2A and 2B show examples of graphical representations of a graph schema for generating chronology-aware data structures in accordance with one illustrative embodiment.
Figure 2B:
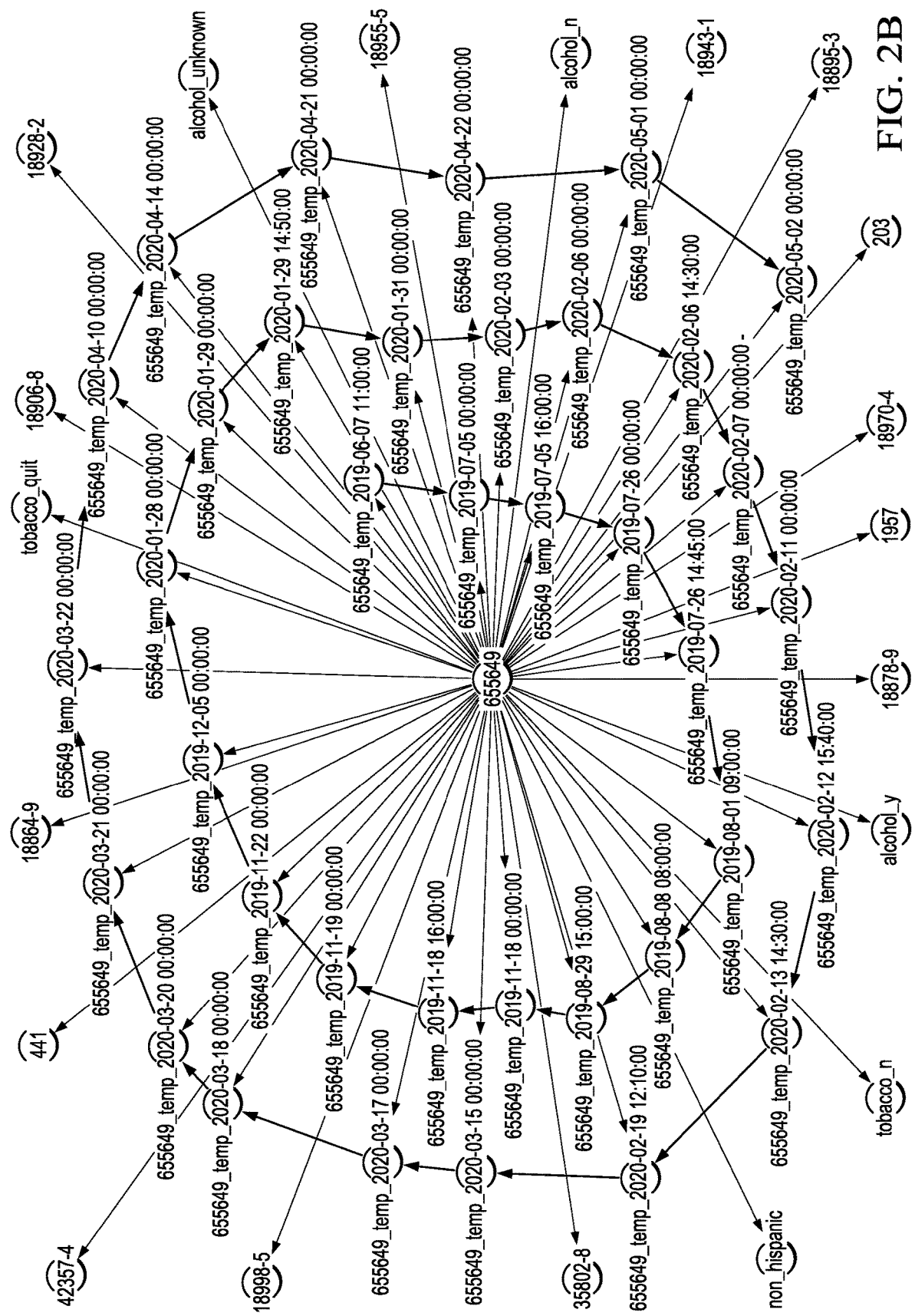

FIGS. 2A and 2B show examples of graphical representations of a graph schema for generating chronology-aware data structures in accordance with one illustrative embodiment. FIG. 2A shows a first graphical representation highlighting the patient-centric graph schema with different vertex (node) types. FIG. 2B shows a second graphical representation highlighting the chronology-aware nature of the graph schema in which encounter nodes are connected by directed edges specifying the chronology ordering of encounters from oldest to newest.

As shown in FIGS. 2A and 2B, the graph schema uses a schema that models the patient data and encounters with the patient as nodes, with edges representing encounter events connecting patients to encounters. In the depiction in FIG. 2A, for example, central vertex (node) types of the graph schema are a patient vertex (node) type 210 and the encounter vertex (node) type 220. Patient related data, e.g., patient birth year, gender, age, ethnicity, etc., are directly connected to the patient vertex type 210 as feature nodes. Encounter related data, e.g., medical codes associated to the findings of the encounter, are directly connected to the encounter vertex type 220 as feature nodes. A patient may have multiple encounters that happen along a timeline, and this information is needed in order to retrieve the temporal progression between two vertices. In order to make use of the chronological information at inference efficiently, the chronology of encounters is modelled as edges in the graph data structure of FIGS. 2A and 2B, binding patients encounters. An example of these edges is shown in FIG. 2A as the edge 230 circling back to the encounter node 220. However, these edges may be more easily seen in FIG. 2B which shows a spiraling set of directed encounter edges spiraling away from an oldest encounter to a newest encounter. These encounter edges allow navigation of searches and analytics along a timeline through simple selective inference, instead of multiple joins per chronological step needed in the common data model.

Referring again to FIG. 1, as noted above, based on this graph schema and the generation of such chronology-aware graph data structures 120, the mechanisms of the illustrative embodiments further provide the above described CGQ engine 130 that provides logic for executing CGQs on the chronology-aware graph data structures 120 to gather features of patients and patient encounters for purposes of generating visual analytic outputs, such as in the form of Sankey diagrams or the like, as described hereafter. An example of the CGQ algorithm that may be implemented using the CGQ engine 130 logic, in accordance with one illustrative embodiment, is depicted in FIG. 3.

As shown in the example algorithm of FIG. 3, the CGQ engine 130 logic operates to address the following query abstraction: gather all the features associated to encounters happening between the presence of feature START_V and the first occurrence of feature END_V for all patients within a maximum time period of t days; keeping the information about which patient is associated to which set of features and keeping the information about the time when the features are recorded. In this example, a prerequisite for operation of the algorithm of FIG. 3 is a chronology-aware graph data structure that is structured as described above, where a significant advantage is achieved in the time-cost associated with executing a query to gather the data for progression evaluation. As shown in FIG. 3, the algorithm involves executing the function RETRIEVE_PATH(vertex_to_explore) on a given chronology-aware graph data structure, where the initial function input is (vertex_to_explore=START_V). The function retrieves features of the care pathways from the start vertex to the end vertex where the care pathways are defined by a sequence or chronology of patient encounters. These care pathways are stored in the stored paths and maintain the associations of the features of the various encounters of the pathways with the corresponding patients while maintaining the temporal or chronology information. At the same time, vertices that are not encounters, i.e., the vertex_type(next_vertx) does not equal "encounter", then the next vertex is stored in the stored_neighbors. Both the stored pathways and the stored neighbors are returned.

Thus, the mechanisms of the illustrative embodiments provide a chronology-aware data structure generation mechanism and chronology-aware graph query mechanism. In addition, the illustrative embodiments provide a pattern discovery and visualization engine 140 based on the chronology-aware graph data structure generation and chronology-aware query mechanism. The pattern discovery and visualization engine 140 operates based on an initial set of features for which meaningful patterns are to be found in the gathered feature instances, e.g., data elements extracted, by the chronology-aware graph data structure generation engine 116, from patient EHR data that match features of the ontology data structure(s) 111 and stored in the database 120, and are within the time frame as determined by the chronology-aware graph query engine 130. In some illustrative embodiments, this initial set of features may be all of the features contained in the results generated by the CGQ engine 130, e.g., the features stored in the stored_neighbors data structure(s) for the encounters in the stored paths data structure, which represents the union of all features of all paths retrieved by the CGQ (features originally contained in the stored neighbors data structure).

All of the possible patterns within the initial set of features are generated and structured as a graph where the frequency of a pattern found in the gathered feature data of the chronology-aware data structures (which again may be graph data structures) in database 120, is modeled as a weight of the edges between the vertices. In this graph, nodes are features and edges link the nodes belonging to the same pattern. Edge weights represent the frequency of occurrence of a given feature combination. For example, assume that there are two patterns of features: F1-F2-F3 and F1-F2-F4. The graph data structure for this example of two patterns will contain the following edges: F1-F2, weight=2; F2-F3, weight=1; and F2-F4, weight=1.

The pattern discovery and visualization engine 140 filters the pattern graph in order to select the most frequent patterns for providing visual analytics. Thus, the results generated by the CGQ engine 130 is a list of care paths and corresponding features, and from these, the patterns can be derived. However, the problem is that the number of possible patterns is enormous. Hence the graph of patterns is generated for each query taking the output of the CGQ engine 130. Then the graph of patterns is used to derive the most frequent patterns and while eliminating patterns that are not included in the most frequent patterns, e.g., the top n patterns, where n is a tunable parameter.

For example, in one illustrative embodiment, all the possible patterns are structured as a graph, where the frequency of a pattern is modelled as the weight of the edges between the vertices. The graph is filtered in order to display the most frequent patterns by traversing the vertices for each layer of the graph (where a layer is made of all the graph nodes resulting from one graph traversal step) to identify all the neighbor vertices in the graph and rank the neighbors in descending order based on their edge weights. Then, the top n number of vertices are selected for including in a filtered vertices set. It should be appreciated that there may be millions of nodes and tens of millions of edges in the graph of patterns. Visualizing all of the possible patterns is not feasible and thus, the invention filters the patterns to those that exist between the top n number of vertices, or top n patterns. In this way, a list of patterns is selected from a pattern graph.

In the selection of the top n number of vertices, the value of n may be a monotonically decreasing value that is decreased to prevent oversampling in further layers as the selection process continues. The remaining graph of vertices in the filtered vertices set is then visualized, such as by way of a Sankey diagram where the dimension of the ribbons is proportional to vertex degree. Modelling the patterns as one graph containing the occurrence information as edge metadata makes the solution provided by the illustrative embodiments not subject anymore to memory and time cost issues. Indeed, it has been observed that queries involving up to $10^{\wedge}26$ estimated number of patterns are represented in a graph and ranked in only a few seconds, with pattern graph dimensions on the order of 10 k vertices and 10 million edges.

FIG. 4 is an example diagram of a pattern discovery algorithm implemented by pattern discovery logic of a pattern discovery and visualization engine in accordance with one illustrative embodiment. As shown in FIG. 4, the algorithm, which may be implemented in logic of the pattern discovery and visualization engine 140 in FIG. 1, starts with a filtered set of vertices, filtered_vertices, which initially comprises only the starting vertex, START_V. Then, for each layer in a range of layers, and for each vertex in the filtered vertices set, all the neighbors of the vertex are identified and ranked according to edge weights associated with those neighbors. Then the top n ranked neighbors are selected and stored in memory. Once all the vertices in the set of filtered vertices is processed in this manner, the set of filtered vertices is then updated with the stored neighbors, i.e., the top n ranked neighbors for each vertex in the set of filtered vertices for the current layer, for the layer. This process is repeated for each layer. It should be appreciated that in each iteration for each layer, the vertices that are not contained in the set of filtered vertices are removed.

The resulting frequent patterns are then used by the pattern discovery and visualization engine 140 to generate a visual representation of the frequent patterns, such as a Sankey diagram or the like. This visual representation may be provided via one or more visual analytics outputs 174 that are provided back to the visual analytics client computing system(s) 170 or other source of a visual analytics request 172. The visual representation generated may take many different forms for representing the strength of relationships between concepts, or features, and patterns of such concepts or features. In general, the visual representation represents the strengths of the relationships or associations as graphical representations having dimensions that correspond to the strength of the relationship or association. One example representation is a Sankey diagram in which graphical ribbons connect concepts/features and the dimensions of these ribbons correspond to the strength of the relationship/ association between the concepts/features, e.g., the probability that one concept/feature is connected to the other, the frequency of occurrence of patterns or care pathways involving these concepts/features, etc.

FIG. 5 is an example diagram of a visual analytics graphical representation for a coherent-aware graph query in accordance with one illustrative embodiment. The depiction in FIG. 5 is that of a Sankey diagram showing the strength of relationship/association between various concepts/features of patient encounters for cardiac patients. For example, as shown in FIG. 5, concepts/features are represented as rectangular blocks 510, 520 with labels, such as cardiovascular examination and evaluation, history of artificial heart valve, pre-surgery evaluation, acute pain, etc. having different categories of feature types, e.g., procedure, situation, disorder, finding, etc. These are concepts/features specified in an ontology data structure, with instances of these concepts/features being identified in ingested patient EHR data structures, with these instances being used to evaluate the probabilities or strengths of associations/relationships between these concepts/features in accordance with the frequent patterns, or care paths, identified from the patient EHR data. The ribbons or channels 530, 540 connecting these concepts/features have widths that represent the strengths of relationships/associations between these concepts/features and thus, the probabilities of care paths involving such concepts/features. Thus, for example, looking at the example in FIG. 5, it is more highly likely that a care path involving a cardiovascular examination and evaluation, a pre-operative state, a pre-surgery evaluation, and aortic stenosis, non-rheumatic disorder will occur. The visualization allows the mechanisms of the illustrative embodiments, and users that view the visualization via the mechanisms of the illustrative embodiments, to capture at a glance the dependencies of the events, remembering what is on the left of a node is in the past and what is on the right is in the future in the example visualization. This visualization is not only useful to project a new patient on the resulting information from the historical cohort and hence compare the possible next steps, but also to improve the efficiency of the treatments in the hospital as a whole. For example, from viewing the visualization, one may determine situations where, and the most prevalent reasons why, patients go through pre-surgery evaluations multiple times (i.e., loops in the diagram). Of course, many other evaluations of care pathways may be made by viewing the visualizations generated by the mechanisms of the illustrative embodiments.

Thus, in the visual representation of a visual analytics output 174, various features, or concepts associated with features, are represented and the representation of these features/concepts within the visual representation have dimensions proportional to the probability of occurrence of the features/concepts based on the extracted frequently occurring patterns in which these features/concepts are present. For example, in a visual representation having a Sankey diagram type, such as shown in FIG. 5 and as noted above, the width of the channels or ribbons connecting concepts/features is proportional to the number of occurrences of the concepts/features in the frequently occurring patterns. Thus, connections between concepts/features represented in the visual representation have dimensions that are proportional to the probability of occurrence of the concepts or features given the extracted care paths identified by the operation of the CGQ engine and frequent pattern discovery mechanisms of the illustrative embodiments. Moreover, the concepts/features are ordered in the visual representation with respect to chronology, as represented in the chronology-aware data structures which allows for the capturing, at a glance, the dependencies of events as noted above.

Thus, the illustrative embodiments provide mechanisms to convert patient longitudinal data from patient EHR data structures from one or more patient EHR data source computing systems, into one or more chronology-aware data structures, which may be chronology-aware graph data structures, that link patient features with patient encounter features while maintaining associations between patients and these features and temporal features specifying the chronology of patient encounters. The illustrative embodiments provide mechanisms for performing chronology-aware query processing to identify sets of features of one or more patients corresponding to patient encounters within a given timeframe of a starting point. The illustrative embodiments provide mechanisms to then perform pattern discovery on these identified sets of features to identify the top most frequently occurring features and patterns of features in the chronology-aware query generated sets of features. The illustrative embodiments further provide mechanisms to visually represent the results of such pattern discovery as visual analytics outputs with graphical representations that have dimensions that are based on the frequency of occurrence of patterns and features/concepts.

In addition, again with reference to FIG. 1, the illustrative embodiments further provide a cohort query engine 150. The cohort query engine 150 provides the logic to orchestrate the operation of the other elements shown in FIG. 1, with regard to multiple different cohorts of patient EHR data structures. For illustration purposes, it will be assumed that the process is performed with regard to two different cohorts, but it can be appreciated that the operation can be performed with regard to any number of cohorts of patient EHR data without departing from the spirit and scope of the present invention.

The chronologically aware cohort query engine 150 executes the chronology-aware graph database generator 110, chronology aware-graph query (CGQ) engine 130, and a pattern discovery and visualization engine 140 with regard to defined cohorts of interest. The cohorts may be pre-defined with regard to different input patient EHR databases for different cohorts, or may be generated by categorizing patient EHR data structures from the one or more EHR data structure source computing systems according to predefined categories of patients, e.g., patients that were diagnosed with a Transient Ischaemic Attack (TIA) event within the time frame of 2017-2019 as one cohort, and patients that were diagnosed with a TIA event within the time frame of 2020-2021 as a second cohort. An initial analysis and categorization of patients may be performed when the patient EHR data is ingested to thereby associate the patient EHR data structures with different cohorts of interest. For each cohort, the processes previously described above are implemented to generate chronology-aware graph data structures 120 for the cohorts as well as execute chronology-aware graph queries (CGQs) on these data structures 120 and identify patterns and analytic visualizations for the cohorts.

The cohort query engine 150 presents the resulting graph-based patterns via timestamped care paths with visualizations, such as the Sankey diagrams described previously, e.g., see FIG. 5 described above. That is, similar to the CGQs described previously, the cohort query may be defined by a user or automated process, such as by a subject matter expert via a user interface of the cohort query engine 150, with the following free parameters: the start and/or end vertex of the patient care paths, the maximum time duration (cohort window) of the paths to be retrieved, the type of vertices (see examples in Table 1 hereafter), the length of edges, whether the encounter search is in the past and/or in the future, patient age range, gender, etc., as well as the number of vertices and edges in the visualization. For cohort queries that compare two different cohorts, e.g., a first cohort of patients from the years 2017 to 2019 and a second cohort of patients from the years 2020 to 2021, individual graphical representations are generated for each cohort with the results from both cohorts being presented via the same visualization with the edges color coding which cohort each path came from, and the nodes color coding whether there are any statistically significant differences (test for proportions based on normal (z) test at 0.01 significance level due to the large dataset) for the care paths between the two cohorts. For all of the graphical representations in the visualization, the dimensions of the edges in the graphical representations, e.g., the width of the edges in Sankey diagrams, reflect the prevalence of the care path normalized to the frequency of the target vertex, e.g., END_V or START_V depending on the direction of the query, e.g., in the past or in the future, respectively. The frequency of a vertex is the width of the ribbon or channel, e.g., how many times did the feature appear in the patterns visualized.

With these parameters and visual analytics representations, the illustrative embodiments assist domain experts in exploring a variety of epidemiological cohort exploratory analysis questions. For example, the illustrative embodiments provide mechanisms through which domain experts may investigate one-sided queries for one target vertex, such as queries directed to answering what characteristic(s) (e.g., observation, medical history, and/or surgical history, etc.) do patients in a clinical cohort of interest (selected by age range, gender, and target vertex, e.g., Transient Ischaemic Attack (TIA) disorder) have in a prior or post cohort window (days) relative to a target vertex. Moreover, the illustrative embodiments provide mechanisms through which domain experts may investigate two-sided queries for care paths between two target vertices, such as queries directed to answering what are the common characteristic(s) (clinical care paths) between two different target vertices for a clinical cohort of interest within a given cohort window. Of course, other types of one and two-sided queries may be answered using the mechanisms of the illustrative embodiments, with these being only examples. For both single and two-sided queries, the illustrative embodiments can also visualize and compare patient care paths between different clinical cohorts and ask which path(s) are statistically more or less common between the two cohorts.

As an example, in an application of one illustrative embodiment, a first cohort comprised all patients with a TIA event between September 2018 and December, 2018 and included their encounters between June, 2017 and December 2019. A second cohort comprised all patients with a TIA event between February 2020 and March, 2020 and included their encounters between January 2020 and February 2021. The resulting chronology-aware graph data structures queried using the above CGQ mechanisms resulted in 21 different vertex types, representing different medical features with graphs for the first cohort containing 1,738,091 vertices and 41,538,032 edges, graphs for the second cohort containing 359,504 vertices and 4,868,759 edges. Table 1 shows the distribution of the number of vertices per vertex type as follows:

TABLE 1

Distribution per vertex type of the graphs created from two TIA cohorts.

| Vertex Type | Cohort 2017-2019 | Cohort 2020-2021 |
|---|---|---|
| diagnosis concept_name | 8,656 | 5,185 |
| diagnosis snomed_id | 8,656 | 5,185 |
| encounter | 1,119,601 | 184,572 |
| patient | 12,029 | 2,833 |
| demographic birth_year | 77 | 71 |
| demographic std_gender | 2 | 2 |
| encounter encounter_date | 220,871 | 41,743 |
| encounter std_encounter_type | 54 | 43 |
| habit mapped_question_answer | 10 | 10 |
| medical_history concept_name | 5,282 | 3,060 |
| medical_history snomed_id | 5,282 | 3,060 |
| observation loinc_id | 5,182 | 2,464 |
| observation loinc-value-unit | 232,424 | 67,888 |
| problem_list concept_name | 4,703 | 440 |
| problem_list snomed_id | 4,703 | 440 |
| procedure concept_name | 6,817 | 3,636 |
| procedure cpt_concept_name | 3,386 | 1,631 |
| procedure procedure_code | 3,385 | 1,629 |
| procedure snomed_id | 6,817 | 3,636 |
| surgical_history concept_name | 2,575 | 1,016 |
| surgical_history snomed_id | 2,575 | 1,016 |
| Total number of vertices | 1,738,091 | 359,504 |
| Total number of edges | 41,538,032 | 4,868,759 |

In the example shown in Table 1, it should be appreciated that "snomed" refers to the Systematized Nomenclature of Human Medicine (SNOMED) clinical terms (CT)® standard previously mentioned above. SNOMED CT may be used to define the one or more input ontologies 111 for the mechanisms of the illustrative embodiments, for example. The term "loinc" refers to Logical Observation Identifiers Names and Codes (LOINC)® which is a registered trademark of Regenstrief Institute, Inc.

To demonstrate the graph visual analytics platform for TIA, various CGQ queries on three example comparison cohorts were performed, as described below. That is, the illustrative embodiments can assist domain experts in exploring a variety of epidemiological cohort exploratory analysis questions which may be represented as CGQ queries. Examples of these CGQ queries include:
1. One sided queries for a single target vertex, e.g., what characteristic(s)(e.g., observation, medical history, and/or surgical history, etc.) do patients in a clinical cohort of interest (e.g., selected by age range, gender, and target vertex, such as TIA disorder for example) have in the prior or post-chort window (days) relative to a target vertex?
2. Two sided queries for care paths between two target vertices, e.g., what are the common characteristic(s) (clinical care paths) between two different target vertices for a clinical cohort of interest within a given cohort window?
3. For both type 1 and 2 queries above, can also ask to visual and compare clinical cohorts and ask which path(s) are statistically more or less common between the two cohorts.

The clinical intention for these queries is to explore differences in patient characteristics (e.g., diagnoses) between cohorts and changes in management practices (e.g., procedures) across time. The example involves a first comparison, shown in FIGS. 6A-6C, that visualizes common disorders of patients diagnosed with a TIA event, within one year before the TIA event, and compares the results from two predefined cohorts: age group 50-70 and age group 70-90. In addition, the example involves a second comparison that visualizes care paths of patients diagnosed with a TIA event within one year before the TIA event, and compares results from two predefined cohorts: patients with recurring TIA and patients with unique TIA events. Moreover, the example involves a third comparison that visualizes care paths of patients diagnosed with TIA in the 6 months after a TIA event, and compares results from two predefined cohorts: March, 2019 to March, 2020 (referred to as pre-pandemic) and March, 2020 to February, 2021 (referred to as during-pandemic) cohort windows.

Figure 6A:
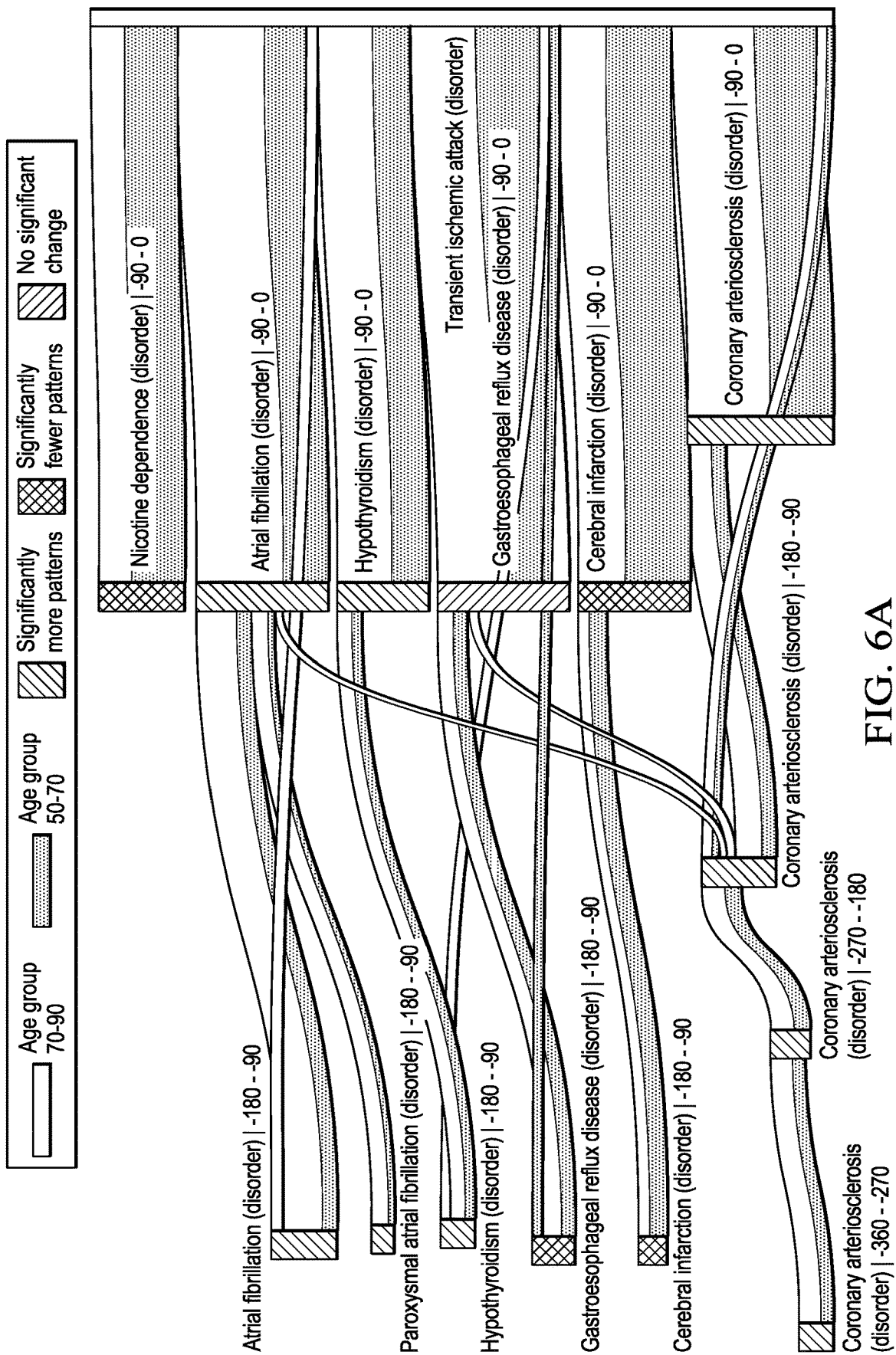
FIGS. 6A-6C are examples of visual analytics graphical representations for three cohort comparisons in accordance with one illustrative embodiment.
Figure 6B:
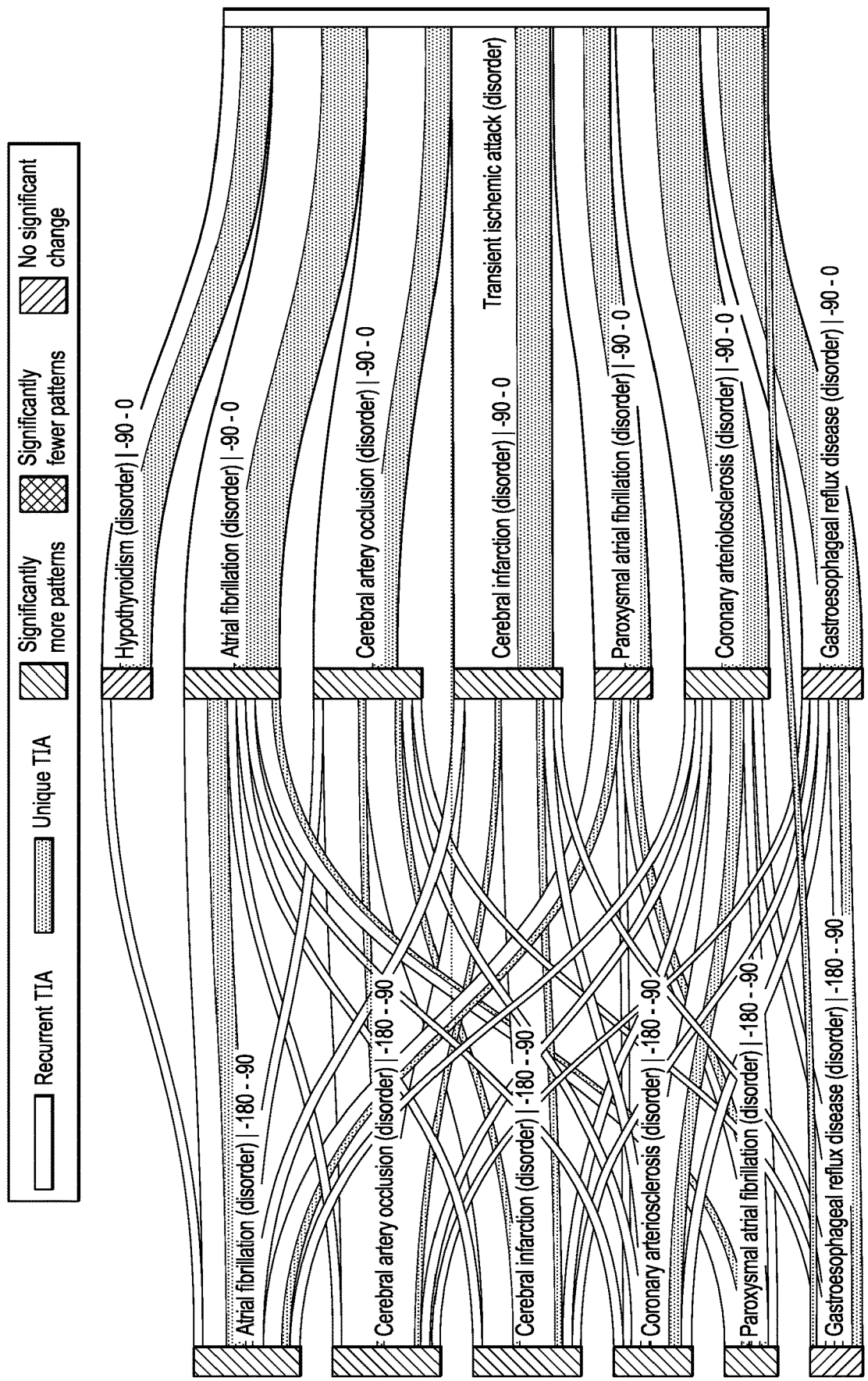
Figure 6C:
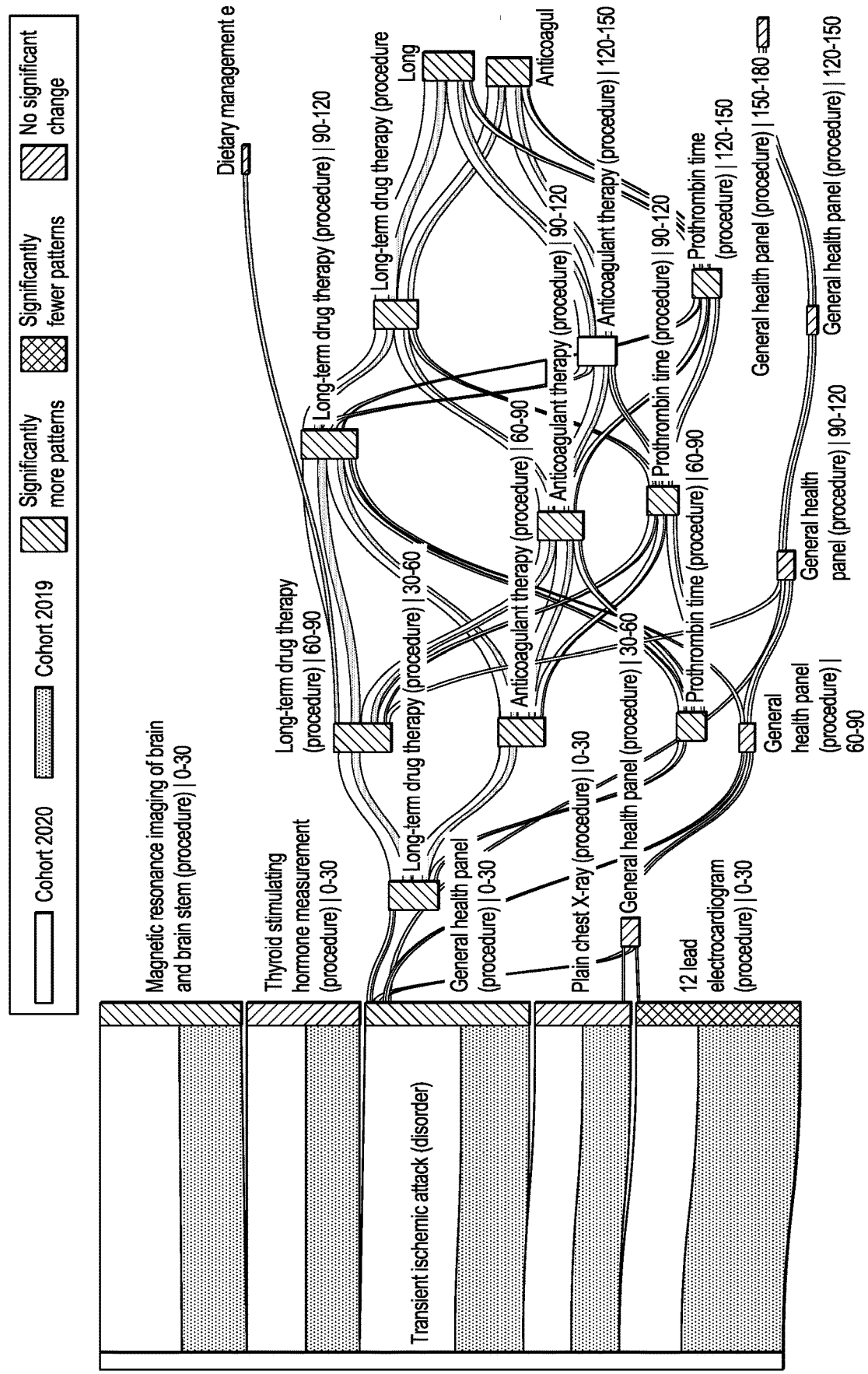

FIGS. 6A-6C are examples of visual analytics graphical representations for three cohort comparisons in accordance with one illustrative embodiment. In each of the visual analytics graphical representations shown in FIGS. 6A-6C, the rectangular elements corresponding to concepts/features of patient encounters are shaded with regard to the number of patterns, or care pathways, in which these concepts/features were determined to be present. In the depicted examples, blocks are shaded based on their statistical significance, where statistical significance is related to the result of a normal test, e.g., p-value<0.01, then significant. In each of these visual analytics graphical representations, the widths of the ribbons or channels indicates the prevalence of patterns involving the connected concepts/features and thus, the relative probability of these care pathways occurring. Moreover, the ordering of the concepts/features relative to each other from a left-to-right ordering indicates a chronology of these concepts/features in care pathways.

FIG. 6A illustrates a visual analytics graphical representation, in the form of a Sankey diagram, in which common main disorders of patients with TIA during the year before the TIA event are shown with regard to a first cohort or grouping of patients aged 50-70 (dark shaded ribbons/channels) and a second cohort or grouping of patients aged 70-90 (light shaded ribbons/channels). FIG. 6B illustrates a visual analytics graphical representation, in the form of a Sankey diagram, in which common main disorders of patients with TIA happening once (first cohort), i.e., a unique TIA event (dark shaded ribbons/channels) and patients with recurrent TIA events (second cohort; light shaded ribbons/channels) are depicted. FIG. 6C illustrates a visual analytics graphical representation, in the form of a Sankey diagram in which common main procedures happening for patients after a first TIA event are depicted. FIG. 6C shows a first cohort of patients which are pre-pandemic, i.e. cohort 2019, using dark shaded ribbons/channels, and a second cohort of patients that are during pandemic, i.e. cohort 2020, using light shaded ribbons/channels. IT should be appreciated that the concepts/features depicted in FIGS. 5-6C are all concepts/features specified in ontology data structures, such as ontology data structure 111 in FIG. 1, and which are used to identify data elements or feature instances in patient EHR data structures in the manner previously described above, from which frequently occurring patterns are identified to generate visual analytics representations such as those depicted in these figures.

Figure 7:
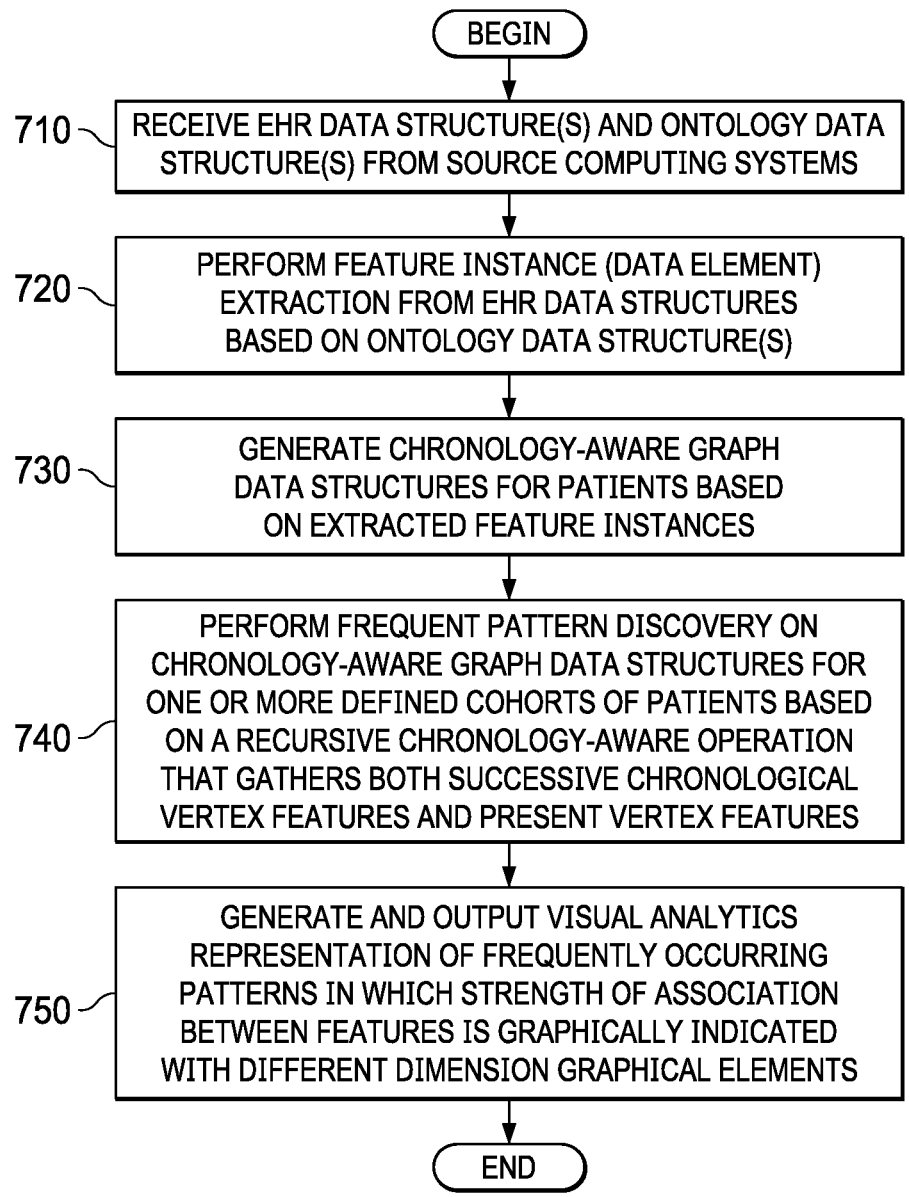
FIG. 7 is a flowchart outlining an example operation of a scalable visual analytics pipeline in accordance with one illustrative embodiment.

FIG. 7 is a flowchart outlining an example operation of a scalable visual analytics pipeline in accordance with one illustrative embodiment. The operation outlined in FIG. 7 may be implemented, for example, by the scalable visual analytics pipeline 100 of FIG. 1, which may in turn be part of a decision support computing system, for example. The operations shown in FIG. 7 are intended to be implemented automatically by computer logic specifically configured to implement the primary operational elements of the pipeline 100 in FIG. 1, e.g., the chronology-aware graph database generator 110, the chronology aware graph database 120, the chronology-aware graph query engine 130, the pattern discovery and visualization engine 140, and the cohort query engine 150. This computer logic may be implemented as software executing on computer hardware and specifically configuring that computer hardware to perform the operations and functions of these various operational elements, dedicated computer hardware logic specifically configured to perform the operations and functions of these various operational elements, or any combination of executed software and/or dedicated hardware.

As shown in FIG. 7, the operation starts by receiving electronic health record (EHR) data structures from an EHR data source computing system and one or more ontology data structures from one or more ontology data source computing systems (step 710). Feature instance, or data element, extraction is performed on the EHR data structures based on the concepts/features specified in the ontology data structure(s) (step 720). Chronology-aware graph data structures for the patients in the EHR data structures are generated based on the extracted concept/feature instances (step 730). Frequent pattern discovery is performed on the chronology-aware graph data structure(s) for one or more defined cohorts of patients based on a recursive chronology-aware operation that gathers both successive chronological vertex features and present vertex features for each iteration (step 740). The features gathered for each pairing of current and successive chronological vertex are then used to generate and output a visual analytics representation of frequently occurring patterns in which the strength of association between features is graphically indicated with different dimension graphical elements, e.g., different width ribbons/channels connecting the features (step 750). The operation then terminates.

From the above description, it can be appreciated that the illustrative embodiments provide mechanisms for the creation of Visual Analytics from large longitudinal datasets containing the following novel elements. The illustrative embodiments provide improved computing tools to generate explicit chronological graph representations of patient healthcare trajectories from structured and/or unstructured electronic health record data. The illustrative embodiments provide improved computing tools that can express a range of common epidemiological style health pattern discovery questions and more efficiently retrieve patient care pathways than multiple join operation based common data models used in patient electronic health record databases, while coping with tens of thousands of patients with historical data spanning many years. Furthermore, the illustrative embodiments provide improved computing tools that implement a graph-based visual analytics pipeline that presents query results across time as visual representations depicting frequency of patterns of extracted concepts/features from patient electronic health records, such as in the form of one or more Sankey graph visualization (SVG) diagrams, for example, which allows for interactive pattern discovery by domain experts.

As described above, the illustrative embodiments of the present invention are specifically directed to an improved computing tool that automatically generates visual analytics representations of input data to assist with decision support operations and various interactive pattern discovery operations of domain experts. While the improved computing tool may be utilized by and may interact with human beings, the actual operations of the scalable visual analytics pipeline mechanisms are intended to be performed in an automated manner using automated processes without human intervention other than potentially receiving user input specifying a desired query to be resolved and providing an output usable by the human being. Moreover, while human beings, e.g., a patient, may be the subject of the patient EHR data structures, the illustrative embodiments of the present invention are not directed to actions performed by the patient or by the user submitting queries, but rather logic and functions performed specifically by the improved computing tool on the patient EHR data structures in accordance with the parameters specified in the queries. Moreover, even though the present invention may provide an output to a visual analytics and/or decision support system that ultimately assists human beings in evaluating the medical conditions of patients, the illustrative embodiments of the present invention are not directed to actions performed by the human being viewing the results of the processing performed by the visual analytics or decision support system, but rather to the specific operations performed by the specific improved computing tool of the present invention which facilitate the generation of visual analytics representations in an improved manner Thus, the illustrative embodiments are not organizing any human activity, but are in fact directed to the automated logic and functionality of an improved computing tool.

Figure 8:
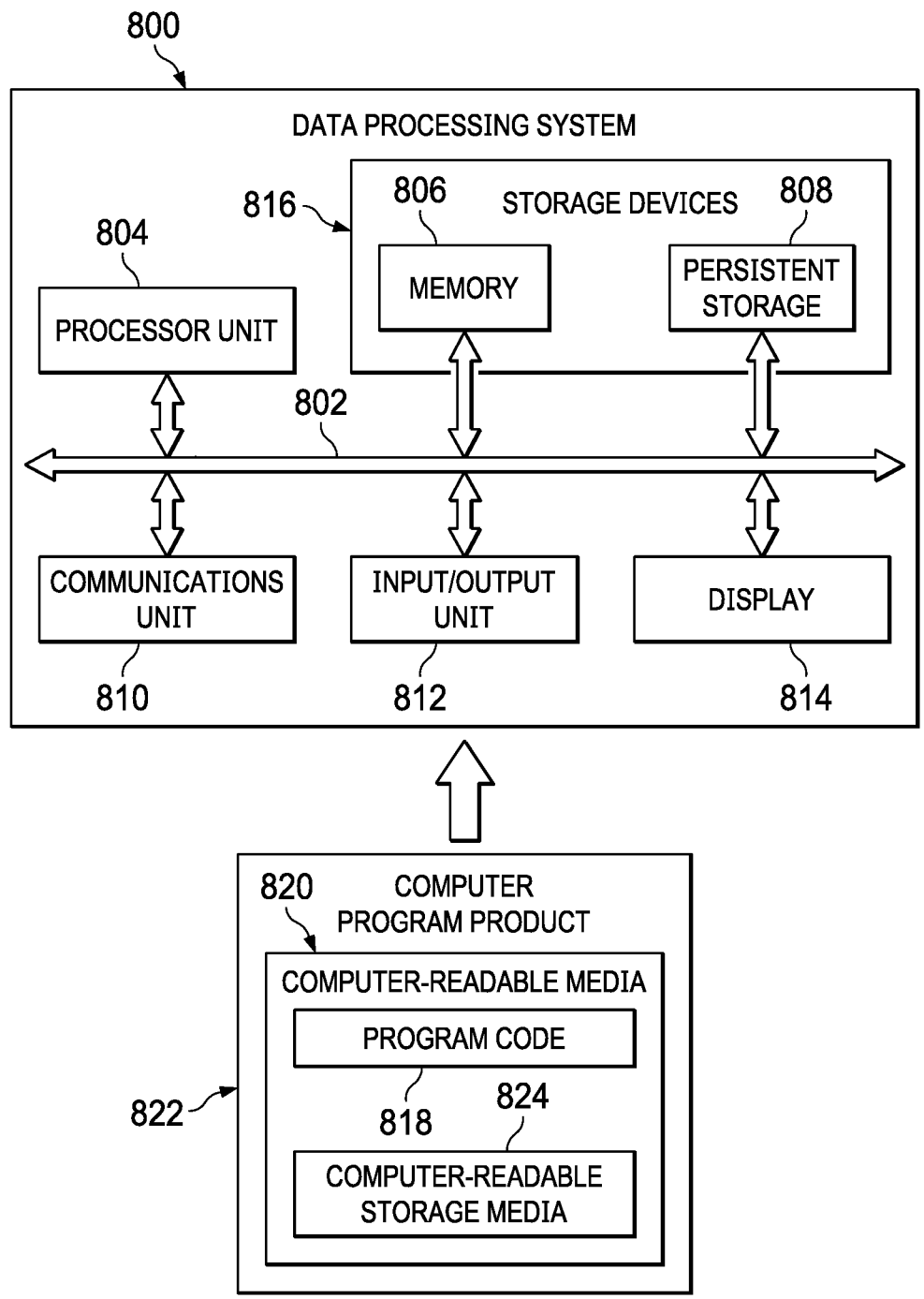
FIG. 8 is a block diagram of an example data processing system in which aspects of the illustrative embodiments are implemented.

Turning now to FIG. 8, a block diagram of a data processing system is depicted in accordance with one illustrative embodiment. Data processing system 800 can be used to implement a server computing device, such as oner or more server computing devices that may be specifically configured to implement the scalable visual analytics pipeline 100 in FIG. 1. It should be appreciated that the pipeline 100 may be implemented on a single server computing device or may be distributed across multiple server computing devices, such as in a server farm or cloud computing implementation, for example. Moreover, the data processing system 800 in FIG. 8 may also be used to implement client computing devices, such as client computing device 170 in FIG. 1. The diagram in FIG. 8 is only intended to be an example and is not intended to be limiting on any type or hardware configuration of the computing devices with which the illustrative embodiments may be implemented.

In this illustrative example, data processing system 800 includes communications framework 802, which provides communications between processor unit 804, memory 806, persistent storage 808, communications unit 810, input/output (I/O) unit 812, and display 814. In this example, communications framework 802 takes the form of a bus system.

Processor unit 804 serves to execute instructions for software that can be loaded into memory 806. Processor unit 804 includes one or more processors. For example, processor unit 804 can be selected from at least one of a multicore processor, a central processing unit (CPU), a graphics processing unit (GPU), a physics processing unit (PPU), a digital signal processor (DSP), a network processor, or some other suitable type of processor. Furthermore, in some illustrative embodiments, processor unit 804 can may be implemented using one or more heterogeneous processor systems in which a main processor is present with secondary processors on a single chip. As another illustrative example, processor unit 804 can be a symmetric multi-processor system containing multiple processors of the same type on a single chip.

Memory 806 and persistent storage 808 are examples of storage devices 816 that may comprise software logic that is executed by the processor unit 804 to specifically configure the processor unit 804 to implement one or more of the operational elements of one or more of the illustrative embodiments. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 816 may also be referred to as computer-readable storage devices in these illustrative examples. Memory 806, in these examples, can be, for example, a random-access memory or any other suitable volatile or non-volatile storage device.

Persistent storage 808 may take various forms, depending on the particular implementation. For example, persistent storage 808 may contain one or more components or devices. For example, persistent storage 808 can be a hard drive, a solid-state drive (SSD), a flash memory, a rewritable optical disk, a rewritable magnetic tape, or some combination of the above. The media used by persistent storage 808 also can be removable. For example, a removable hard drive can be used for persistent storage 808.

Communications unit 810, in these illustrative examples, provides for communications with other data processing systems or devices. In these illustrative examples, communications unit 810 is a network interface card through which data communications with one or more data networks may be implemented, such as the data network depicted in FIG. 1.

Input/output unit 812 allows for input and output of data with other devices that can be connected to data processing system 800. For example, input/output unit 812 may provide a connection for user input through at least one of a keyboard, a mouse, or some other suitable input device. Further, input/output unit 812 may send output to a printer. Display 814 provides a mechanism to display information to a user.

Instructions for at least one of the operating system, applications, or programs can be located in storage devices 816, which are in communication with processor unit 804 through communications framework 802. The processes of the different embodiments can be performed by processor unit 804 using computer-implemented instructions, which may be located in a memory, such as memory 806. These instructions are referred to as program code, computer usable program code, or computer-readable program code that can be read and executed by a processor in processor unit 804. The program code in the different embodiments can be embodied on different physical or computer-readable storage media, such as memory 806 or persistent storage 808.

Program code 818 is located in a functional form on computer-readable media 820 that is selectively removable and can be loaded onto or transferred to data processing system 800 for execution by processor unit 804. Program code 818 and computer-readable media 820 form computer program product 822 in these illustrative examples. In the illustrative example, computer-readable media 820 is computer-readable storage media 824.

In these illustrative examples, computer-readable storage media 824 is a physical or tangible storage device used to store program code 818 rather than a medium that propagates or transmits program code 818. Alternatively, program code 818 can be transferred to data processing system 800 using a computer-readable signal media. The computer-readable signal media can be, for example, a propagated data signal containing program code 818. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection. Thus, computer-readable storage media 824 are non-transitory tangible storage media different from, and not including, transitory computer readable signal media.

The different components illustrated for data processing system 800 are not meant to provide architectural limitations to the manner in which different embodiments can be implemented. In some illustrative examples, one or more of the components may be incorporated in or otherwise form a portion of, another component. For example, memory 806, or portions thereof, may be incorporated in processor unit 804 in some illustrative examples. The different illustrative embodiments can be implemented in a data processing system including components in addition to or in place of those illustrated for data processing system 800. Other components shown in FIG. 8 can be varied from the illustrative examples shown. The different embodiments can be implemented using any hardware device or system capable of running program code 818.

Thus, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to specifically configure the at least one processor to implement a visual analytics pipeline that performs the method comprising:

generating, by a chronology aware graph data structure generator of the visual analytics pipeline, from an input database of records, a chronology-aware graph data structure of a plurality of records based features specified in an ontology data structure, wherein the chronology-aware graph data structure comprises vertices representing one or more of events or records based features corresponding to the events, and edges representing chronological relationships between the events;

executing, by a chronology aware graph query engine of the visual analytics pipeline, a chronology-aware graph query on the chronology-aware graph data structure to generate a filtered set of vertices and corresponding features corresponding to criteria of the chronology-aware graph query;

executing, by a pattern discovery and visualization engine of the visual analytics pipeline, a pattern discovery operation on the filtered set of vertices and the corresponding features corresponding to the criteria of the chronology-aware graph query, to identify a subset of vertices and corresponding features that correspond to a relatively higher frequency set of patterns of event paths; and generating, by the pattern discovery and visualization engine, a visual analytics graphical representation, for the subset of vertices and the corresponding features that correspond to the relatively higher frequency set of patterns of the event paths, in a visual analytics output.

2. The method of claim 1, wherein the input database of records is an electronic health record database and the plurality of records is a plurality of patient electronic health records, and wherein the events are patient encounters between a patient and at least one of a healthcare professional or a healthcare facility, and the plurality of records based features comprise clinical features of patients.

3. The method of claim 2, wherein the records based features are medical codes associated with patient electronic healthcare records.

4. The method of claim 1, wherein the input database of records is at least one information technology log database and the plurality of records is a plurality of information technology records specifying events occurring in an information technology environment, and wherein the events are information technology environment events occurring within one or more information technology software or hardware systems.

5. The method of claim 1, wherein the chronology-aware graph query is recursively executed and, during each iteration of the recursive execution, collects features for a current vertex for each iteration and identifies a next vertex along a care path specified in the chronology-aware graph data structure, wherein the collected features for each iteration are combined into the filtered set of vertices and the corresponding features corresponding to the criteria of the chronology-aware graph query.

6. The method of claim 1, wherein executing the pattern discovery operation on the filtered set of vertices and the corresponding features corresponding to the criteria of the chronology-aware graph query comprises:
generating a pattern graph data structure comprising nodes corresponding to the filtered set of vertices and edges connecting vertices of the filtered set of vertices, where each edge connecting vertices of the filtered set of vertices has pattern frequency information specifying a frequency of a pattern comprising connected vertices of each edge;
determining, for each path along the generated pattern graph data structure, a summed pattern frequency along the path; and
processing the generated pattern graph data structure to select a predetermined number of paths of patterns of vertices in the generated pattern graph data structure having a relatively highest ranked summed pattern frequency information.

7. The method of claim 1, wherein generating, from the input database of records, the chronology-aware graph data structure comprises:
correlating feature types specified in the ontology data structure with annotations or labels associated with elements of records in the input database of records;
extracting records based features correlated with feature types specified in the ontology data structure and temporal information associated with the extracted records based features; and
generating the chronology-aware graph data structure based on the extracted records based features and the temporal information.

8. The method of claim 1, wherein the visual analytics graphical representation comprises graphical channels connecting graphical representations of concepts corresponding to vertices in the subset of vertices, wherein each channel in the graphical channels has a width proportional to a probability of occurrence of a corresponding pattern of care paths comprising connected concepts corresponding to the channel.

9. The method of claim 8, wherein, for each channel in the graphical channels, the graphical representations of concepts are organized in the visual analytics graphical representation according to a chronology of encounters of the corresponding pattern of care paths.

10. The method of claim 1, wherein the visual analytics pipeline is part of an artificial intelligence decision support computing system and provides the visual analytics graphical representation in a graphical user interface having user interface controls to evaluate a range of epidemiological health pattern discovery questions based on the visual analytics graphical representation.

11. A computer program product comprising a computer readable storage medium having a computer readable program stored therein, wherein the computer readable program, when executed in a data processing system, causes the data processing system to implement a visual analytics pipeline which operates to:
generate, by a chronology aware graph data structure generator of the visual analytics pipeline, from an input database of records, a chronology-aware graph data structure of a plurality of records based features specified in an ontology data structure, wherein the chronology-aware graph data structure comprises vertices representing one or more of events or records based features corresponding to the events, and edges representing chronological relationships between the events;
execute, by a chronology aware graph query engine of the visual analytics pipeline, a chronology-aware graph query on the chronology-aware graph data structure to generate a filtered set of vertices and corresponding features corresponding to criteria of the chronology-aware graph query;
execute, by a pattern discovery and visualization engine of the visual analytics pipeline, a pattern discovery operation on the filtered set of vertices and the corresponding features corresponding to the criteria of the chronology-aware graph query, to identify a subset of vertices and corresponding features that correspond to a relatively higher frequency set of patterns of event paths; and
generate, by the pattern discovery and visualization engine, a visual analytics graphical representation, for the subset of vertices and the corresponding features that correspond to the relatively higher frequency set of patterns of the event paths, in a visual analytics output.

12. The computer program product of claim 11, wherein the input database of records is an electronic health record database and the plurality of records is a plurality of patient electronic health records, and wherein the events are patient encounters between a patient and at least one of a healthcare professional or a healthcare facility, and the plurality of records based features comprise clinical features of patients.

13. The computer program product of claim 12, wherein the records based features are medical codes associated with patient electronic healthcare records.

14. The computer program product of claim 11, wherein the input database of records is at least one information technology log database and the plurality of records is a plurality of information technology records specifying events occurring in an information technology environment, and wherein the events are information technology environment events occurring within one or more information technology software or hardware systems.

15. The computer program product of claim 11, wherein the chronology-aware graph query is recursively executed and, during each iteration of the recursive execution, collects features for a current vertex for each iteration and identifies a next vertex along a care path specified in the chronology-aware graph data structure, wherein the collected features for each iteration are combined into the filtered set of vertices and the corresponding features corresponding to the criteria of the chronology-aware graph query.

16. The computer program product of claim 11, wherein executing the pattern discovery operation on the filtered set of vertices and the corresponding features corresponding to the criteria of the chronology-aware graph query comprises:
generating a pattern graph data structure comprising nodes corresponding to the filtered set of vertices and edges connecting vertices of the filtered set of vertices, where each edge connecting vertices of the filtered set of vertices has pattern frequency information specifying a frequency of a pattern comprising connected vertices of each edge;

determining, for each path along the generated pattern graph data structure, a summed pattern frequency along the path; and processing the generated pattern graph data structure to select a predetermined number of paths of patterns of vertices in the generated pattern graph data structure having a relatively highest ranked summed pattern frequency information.

17. The computer program product of claim 11, wherein generating, from the input database of records, the chronology-aware graph data structure comprises:

correlating feature types specified in the ontology data structure with annotations or labels associated with elements of records in the input database of records;

extracting records based features correlated with feature types specified in the ontology data structure and temporal information associated with the extracted records based features; and generating the chronology-aware graph data structure based on the extracted records based features and the temporal information.

18. The computer program product of claim 11, wherein the visual analytics graphical representation comprises graphical channels connecting graphical representations of concepts corresponding to vertices in the subset of vertices, wherein each channel in the graphical channels has a width proportional to a probability of occurrence of a corresponding pattern of care paths comprising connected concepts corresponding to the channel.

19. The computer program product of claim 18, wherein, for each channel in the graphical channels, the graphical representations of concepts are organized in the visual analytics graphical representation according to a chronology of encounters of the corresponding pattern of care paths.

20. An apparatus comprising:
at least one processor; and
at least one memory coupled to the at least one processor, wherein the at least one memory comprises instructions which, when executed by the at least one processor, cause the at least one processor to implement a visual analytics pipeline which operates to:

generate, by a chronology aware graph data structure generator of the visual analytics pipeline, from an input database of records, a chronology-aware graph data structure of a plurality of records based features specified in an ontology data structure, wherein the chronology-aware graph data structure comprises vertices representing one or more of events or records based features corresponding to the events, and edges representing chronological relationships between the events;

execute, by a chronology aware graph query engine of the visual analytics pipeline, a chronology-aware graph query on the chronology-aware graph data structure to generate a filtered set of vertices and corresponding features corresponding to criteria of the chronology-aware graph query;

execute, by a pattern discovery and visualization engine of the visual analytics pipeline, a pattern discovery operation on the filtered set of vertices and the corresponding features to identify a subset of vertices and the corresponding features corresponding to the criteria of the chronology-aware graph query that correspond to a relatively higher frequency set of patterns of event paths; and generate, by the pattern discovery and visualization engine, a visual analytics graphical representation, for the subset of vertices and the corresponding features that correspond to the relatively higher frequency set of patterns of the event paths, in a visual analytics output.

* * * * *